United States Patent
Tajiri et al.

(10) Patent No.: US 8,222,613 B2
(45) Date of Patent: Jul. 17, 2012

(54) SCANNING IRRADIATION DEVICE OF CHARGED PARTICLE BEAM

(75) Inventors: Shinya Tajiri, Tokyo (JP); Yuichi Yamamoto, Tokyo (JP); Yuehu Pu, Tokyo (JP); Haruo Yamashita, Shizuoka (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 410 days.

(21) Appl. No.: 12/574,136

(22) Filed: Oct. 6, 2009

(65) Prior Publication Data

US 2010/0090123 A1 Apr. 15, 2010

(30) Foreign Application Priority Data

Oct. 15, 2008 (JP) ................... 2008-266275

(51) Int. Cl.
- *G01K 1/08* (2006.01)
- *H01J 3/14* (2006.01)
- *H01J 3/26* (2006.01)

(52) U.S. Cl. .............. 250/398; 250/495.1; 250/396 ML; 250/493.1; 250/492.1

(58) Field of Classification Search .................. 250/398, 250/495.1, 396 ML, 493.1, 492.1
See application file for complete search history.

(56) References Cited

U.S. PATENT DOCUMENTS

| | | | |
|---|---|---|---|
| 6,246,066 B1 * | 6/2001 | Yuehu | 250/492.3 |
| 2002/0030164 A1 | 3/2002 | Akiyama et al. | |
| 2003/0141460 A1 * | 7/2003 | Kraft | 250/492.1 |
| 2008/0197296 A1 * | 8/2008 | Uematsu | 250/492.3 |

FOREIGN PATENT DOCUMENTS

| | | |
|---|---|---|
| JP | 10-263098 A | 10/1998 |
| JP | 11-242100 A | 9/1999 |
| JP | 11-309220 A | 11/1999 |
| JP | 2002-113118 A | 4/2002 |
| JP | 2003-528659 A | 9/2003 |

* cited by examiner

*Primary Examiner* — Jack Berman
*Assistant Examiner* — Meenakshi Sahu
(74) *Attorney, Agent, or Firm* — Buchanan Ingersoll & Rooney PC (57) ABSTRACT

An inexpensive scanning irradiation device of a particle beam is obtained without using a rotating gantry. A first scanning electromagnet and a second scanning electromagnet, whose deflection surfaces of the particle beam are the same, and which bend the particle beam having an incident beam axis angle of approximately 45 degrees relative to a horizontal direction in reverse directions to each other; an electromagnet rotation driving mechanism which integrates the first and the second scanning electromagnets and rotates these scanning electromagnets around the incident beam axis; and a treatment bed are provided. The particle beam deflected by the first and the second scanning electromagnets can be obtained at a range of −45 degrees to +45 degrees in deflection angle from an incident beam axis direction.

12 Claims, 10 Drawing Sheets

SCANNING IRRADIATION DEVICE OF CHARGED PARTICLE BEAM

BACKGROUND OF THE INVENTION

1. Field of the Invention

The present invention relates to a scanning irradiation device of a charged particle beam, in which a charged particle beam emitted from an accelerator is deflected by a first scanning electromagnet and a second scanning electromagnet and is irradiated to an irradiation target.

2. Description of the Related Art

A scanning irradiation device of a charged particle beam in known particle beam therapy systems includes an accelerator which emits a charged particle beam (for example, beam of electron, proton, and heavy ion); a group of electromagnets such as quadrupole electromagnets and deflection electromagnets which transport abeam taken out from the accelerator; two scanning electromagnets (scanning electromagnet pair) in which beam deflection surfaces are located on the same surface, and excited in opposite polarity to each other; a magnet rotation driving mechanism which rotates the scanning electromagnet pair around an incident beam axis; a range shifter which degrades beam energy and stops a beam at any depth in the inside of the body by taking in and out a plurality sheets of plates made of a material such as polyethylene or the like having density equivalent to water and being different in thickness on the incident beam axis; a scanning irradiation control device which performs control of the scanning electromagnet pair and the range shifter; a recumbent position treatment bed which is a flat bed; and a treatment bed driving mechanism which moves the recumbent position treatment bed to any position. Further, the scanning irradiation device of the charged particle beam is composed of a rotational structure (rotating gantry) mounted with the group of electromagnets which transport the beam, the scanning electromagnet pair, the magnet rotation driving mechanism, the range shifter, and the scanning irradiation control device; and a gantry rotating mechanism which determines an irradiation direction to an irradiation target.

Next, the operation will be described. A patient is mounted on the recumbent position treatment bed, the patient is moved to any position by the treatment bed driving mechanism, and the patient's position is adjusted so as to correctly irradiate a beam to the irradiation target. The beam taken out from the accelerator is deflected by the scanning electromagnet on the upper stream side to a direction deviating from the incident beam axis, deflected in an opposite direction by the scanning electromagnet on the lower stream side, and finally, irradiated to the irradiation target parallel to the incident beam axis. Two scanning electromagnets on the upper stream side and the lower stream side are integrated and rotated at any angle around the incident beam axis; and therefore, the beam is distributed and irradiated to the irradiation target in any shape of two-dimensional flat surface.

Next, the range shifter takes in and out the plurality of plates having the density equivalent to water and being different in thickness; and accordingly, energy of the beam is attenuated to any energy, depth at which the beam is stopped is changed, similarly the beam is distributed in any shape of two-dimensional flat surface, and the beam is irradiated. As described above, a spot of the beam is three-dimensionally arranged; and accordingly, irradiation is performed to the irradiation target in a uniform radiation dose distribution in accordance with its three-dimensional shape. In the scanning irradiation control device, the aforementioned series of movements is controlled so that the respective apparatuses operate in cooperation.

When important organs which do not have to be irradiated are located in the vicinity of the irradiation target, there is a difficult case to give sufficient radiation dose to the irradiation target by only irradiation from one direction while suppressing the radiation dose to the important organs. In this case, the group of electromagnets which transport the beam, the scanning electromagnet pair, and the range shifter are integrated to the rotational structure (rotating gantry), and the rotating gantry is rotated; and accordingly, irradiation (referred to as multiple field irradiation) is performed from a plurality of arbitrary angle directions so as to avoid the irradiation to the important organs. Incidentally, as a known art related to the aforementioned scanning irradiation device of the charged particle beam, there are the following patent documents: Japanese Unexamined Patent Publication No. 10-263098, Japanese Unexamined Patent Publication No. 11-309220, and Japanese Unexamined Patent Publication No. 2002-113118. In the case of performing the multiple field irradiation in order to suppress radiation dose to the important organs to be low, the known scanning irradiation device of the charged particle beam needs the rotating gantry which integrally rotates with beam line apparatuses such as the group of electromagnets of the quadrupole electromagnets, the deflection electromagnets, and the like, which transport the beam; the scanning electromagnets; and the range shifter. The rotating gantry is of the rotational structure having a diameter of approximately 10 m; and therefore, the rotating gantry becomes an expensive irradiation device.

SUMMARY OF THE INVENTION

An object of the present invention is to solve the foregoing problem and to provide an inexpensive scanning irradiation device of a charged particle beam without using a rotating gantry.

According to the present invention, there is provided a scanning irradiation device of a charged particle beam, which includes: a first scanning electromagnet and a second scanning electromagnet located at the lower stream of the first scanning electromagnet, whose deflection surfaces of a charged particle beam are the same, and whose excitations are controlled so as to bend the charged particle beam having an incident beam axis angle of approximately 45 degrees relative to a horizontal direction in reverse directions to each other; an electromagnet rotation driving mechanism which integrates the first and the second scanning electromagnets and rotates these scanning electromagnets around the incident beam axis; a scanning irradiation control device which performs control of the excitations of the first and the second scanning electromagnets and performs control of the rotation of the electromagnet rotation driving mechanism; and a treatment bed which is moved to the lower stream of the second scanning electromagnet and is installed so that a direction orthogonal to a flat surface, the surface being in a direction perpendicular to a floor and including the incident beam axis, becomes a body axis direction of a patient. The first and the second scanning electromagnets are configured such that a maximum deflection angle of the second scanning electromagnet is larger than a maximum deflection angle of the first scanning electromagnet, and the charged particle beam deflected by the first and the second scanning electromagnets can be obtained at a range of −45 degrees to +45 degrees in deflection angle from the incident beam axis direction.

Furthermore, according to the present invention, there is provided a scanning irradiation device of a charged particle beam, which includes: a first scanning electromagnet and a second scanning electromagnet located at the lower stream of the first scanning electromagnet, whose deflection surfaces of a charged particle beam are the same, and whose excitations are controlled so as to bend the charged particle beam having a first incident beam axis angle of approximately 22.5 degrees relative to a horizontal direction in reverse directions to each other; a first electromagnet rotation driving mechanism which integrates the first and the second scanning electromagnets and rotates these scanning electromagnets around the first incident beam axis; a third scanning electromagnet and a fourth scanning electromagnet located at the lower stream of the third scanning electromagnet, whose deflection surfaces of a charged particle beam are the same, and whose excitations are controlled so as to bend the charged particle beam having a second incident beam axis angle of approximately 112.5 degrees relative to the horizontal direction in reverse directions to each other within a flat surface, the surface being in a direction perpendicular to a floor and including the incident beam axis; a second electromagnet rotation driving mechanism which integrates the third and the fourth scanning electromagnets and rotates these scanning electromagnets around the second incident beam axis; a scanning irradiation control device which performs control of the excitations of the first, the second, the third, and the fourth scanning electromagnets, and performs control of the rotations of the first and the second electromagnet rotation driving mechanisms; and a treatment bed which is moved to the lower stream of the second and the fourth scanning electromagnets and is installed so that a direction orthogonal to a flat surface, the surface being in a direction perpendicular to the floor and including the incident beam axis, becomes a body axis direction of a patient. The first and the second scanning electromagnets are configured so that a maximum deflection angle of the second scanning electromagnet is larger than a maximum deflection angle of the first scanning electromagnet, and the charged particle beam deflected by the first and the second scanning electromagnets can be obtained at a range of −22.5 degrees to +22.5 degrees in deflection angle from the first incident beam axis direction; and the third and the fourth scanning electromagnets being configured so that a maximum deflection angle of the fourth scanning electromagnet is larger than a maximum deflection angle of the third scanning electromagnet, and the charged particle beam deflected by the third and the fourth scanning electromagnets can be obtained at a range of −22.5 degrees to +22.5 degrees in deflection angle from the second incident beam axis direction.

According to a scanning irradiation device of a charged particle beam of the present invention, a direction of patient's recumbent position on a treatment bed, thereby making it possible to irradiate at any angle of 360 degrees relative to a patient's body axis, whereby multiple field irradiation can be performed at any irradiation angle even without using a gantry.

Still furthermore, according to the present invention, there is provided a scanning irradiation device of a charged particle beam, which includes: a first scanning electromagnet and a second scanning electromagnet located at the lower stream of the first scanning electromagnet, whose deflection surfaces of a charged particle beam are the same, and whose excitations are controlled so as to bend the charged particle beam having an incident beam axis angle of approximately 90 degrees relative to a horizontal direction in reverse directions to each other; an electromagnet rotation driving mechanism which integrates the first and the second scanning electromagnets and rotates these scanning electromagnets around the incident beam axis; a scanning irradiation control device which performs control of the excitations of the first and the second scanning electromagnets and performs control of the rotation of the electromagnet rotation driving mechanism; and a sitting position treatment bed which is arranged in a direction perpendicular to a floor at the lower stream of the second scanning electromagnet, and in which a backrest can be inclined back and forth at a range of −45 degrees to +45 degrees. The first and the second scanning electromagnets are configured so that a maximum deflection angle of the second scanning electromagnet is larger than a maximum deflection angle of the first scanning electromagnet, and the charged particle beam deflected by the first and the second scanning electromagnets can be obtained at a range of −45 degrees to +45 degrees in deflection angle from the incident beam axis direction.

In addition, according to a scanning irradiation device of a charged particle beam of the present invention, a backrest of a sitting position treatment bed can be inclined back and forth at a range of −45 degrees to +45 degrees, thereby making it possible to irradiate at any angle above a horizontal level relative to head and neck, whereby an irradiation device capable of performing multiple field irradiation of the head and neck can be supplied inexpensively.

The foregoing and other objects, features, aspects and advantages of the present invention will become more apparent from the following detailed description of the present invention when taken in conjunction with the accompanying drawings.

DETAILED DESCRIPTION OF THE INVENTION

Preferred Embodiment 1

Figure 1:
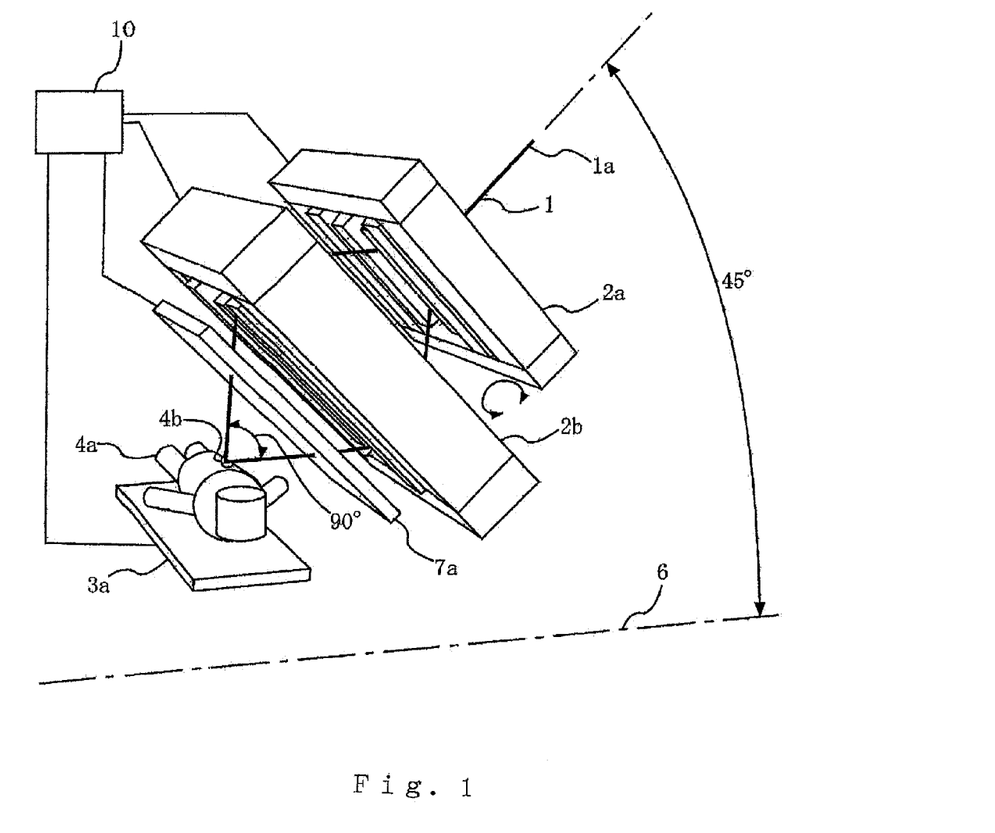
FIG. 1 is a configuration diagram showing a scanning irradiation device of a charged particle beam according to a preferred embodiment 1 of the present invention.

FIG. 1 is a configuration diagram showing a scanning irradiation device of a charged particle beam according to a preferred embodiment 1 of the present invention. A charged particle beam (referred to as beam) 1, which is taken out from an accelerator and is transported via a group of electromagnets such as quadrupole electromagnets and deflection electromagnets, is made incident from an incident beam axis angle of approximately 45 degrees relative to a floor (horizontal direction) 6. A first scanning electromagnet 2a deflects the beam 1 at any angle of a range of −45 degrees to +45 degrees (its range may be exceeded) relative to an incident beam axis 1a. A second scanning electromagnet 2b is arranged at the lower stream of the first scanning electromagnet 2a, has a beam deflection surface which is located on the same surface as that of the first scanning electromagnet 2a, and deflects the beam 1 at any angle of a range of −90 degrees to +90 degrees (its range may be exceeded) in a reverse direction to the first scanning electromagnet 2a. A maximum deflection angle of the second scanning electromagnet 2a is set to be larger than a maximum deflection angle of the first scanning electromagnet 2a, so that the beam 1 is collected at an irradiation target 4b.

An electromagnet rotation driving mechanism 20 (see FIG. 2) integrates the first scanning electromagnet 2a and the second scanning electromagnet 2b and rotates these scanning electromagnets around the incident beam axis 1a. A range shifter 7a is arranged at the lower stream of the second scanning electromagnet 2b, and takes in and out a plurality sheets of plates, which is made of a material such as polyethylene or the like having density equivalent to water and different in thickness, on the incident beam axis 1a; and accordingly, energy of the beam 1 is degraded by a desired amount. Taking in and out of the range shifter 7a on the incident beam axis 1a is controlled by a scanning irradiation control device 10. A recumbent position treatment bed 3a is arranged by being moved to the lower stream of the range shifter 7a, and is installed so that a direction orthogonal to a flat surface, the surface being in a direction perpendicular to the floor and including the incident beam axis 1a, becomes a body axis direction of a patient 4a. The scanning irradiation control device 10 performs control of excitation of the first and the second scanning electromagnets 2a and 2b, the taking in and out of the range shifter 7a, and rotation of the electromagnet rotation driving mechanism 20. Incidentally, the displacement arrangement of the recumbent position treatment bed 3a may be controlled by the scanning irradiation control device 10.

Figure 2:
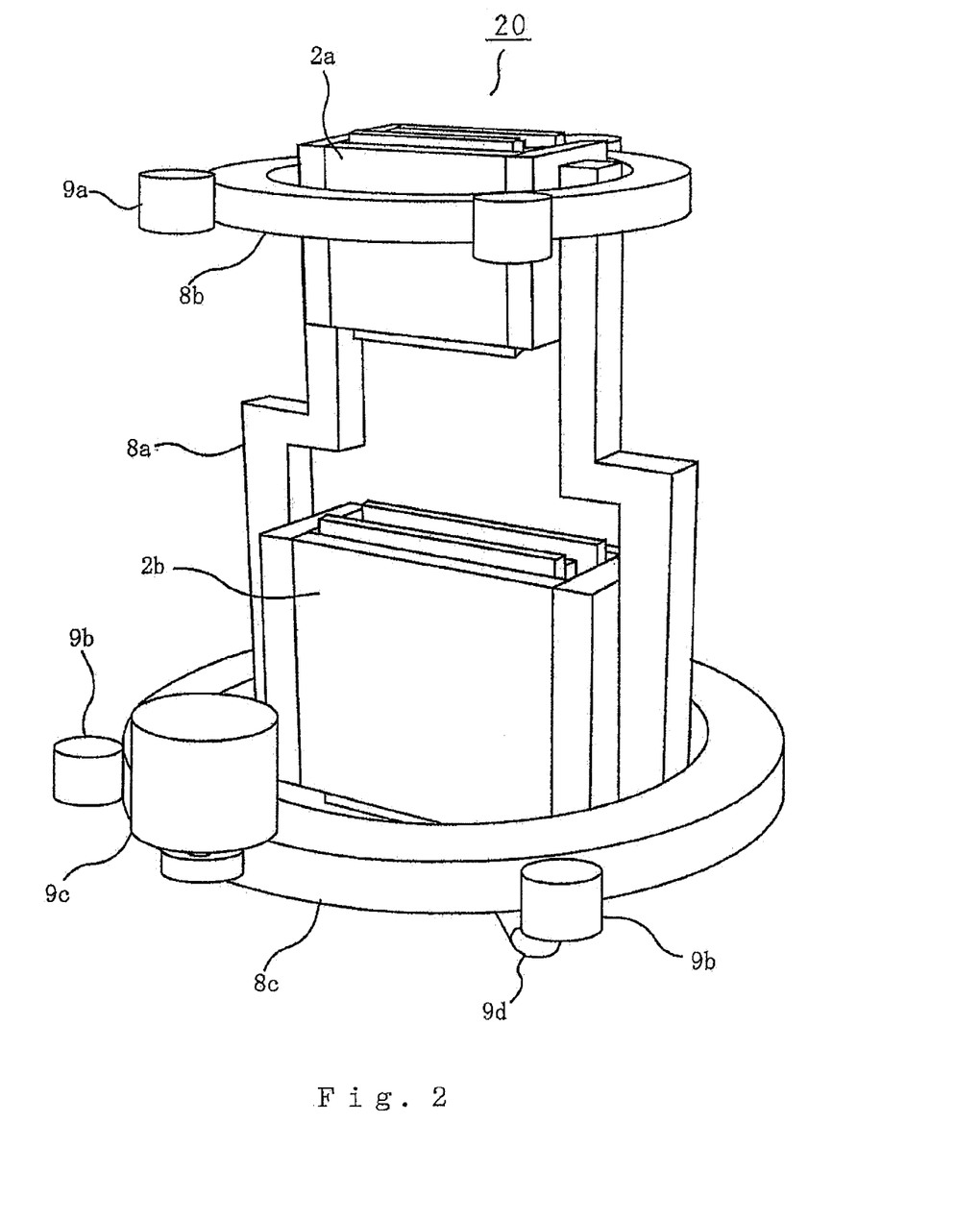
FIG. 2 is a configuration diagram showing an electromagnet rotation driving mechanism in the preferred embodiment 1.

FIG. 2 is a configuration diagram showing the electromagnet rotation driving mechanism 20 in the preferred embodiment 1. The first scanning electromagnet 2a and the second scanning electromagnet 2b are integrally supported by a connecting support 8a so that their beam deflection surfaces are provided on the same surface. The connecting support 8a is fixed to rotational support rings 8b and 8c. The rotational support rings 8b and 8c are retained so as to be rotated by support rollers 9a, 9b, and 9d; and are rotationally driven by a motor 9c which is controlled by the scanning irradiation control device 10.

Next, the operation will be described. The intensity of excitation of the first scanning electromagnet 2a is controlled in a positive or negative direction; and accordingly, the beam 1 made incident at an incident angle of approximately 45 degrees from the floor 6 is deflected within the deflection surface to any angle of a range of −45 degrees to +45 degrees relative to the incident beam axis 1a. Next, the intensity of excitation of the second scanning electromagnet 2b is controlled in a negative or positive direction; and accordingly, the beam 1 is deflected in a reverse direction within the deflection surface (that is, the same surface as the deflection surface of the first scanning electromagnet 2a) to any angle of a range of −90 degrees to +90 degrees. As described above, the beam 1 is irradiated to the irradiation target 4b of the patient within the same deflection surface at any angle of a range of −45 degrees to +45 degrees (its range may be exceeded) relative to the incident beam axis 1a.

The scanning electromagnet 2a and 2b integrally supported by the connecting support 8a are rotationally driven by the scanning irradiation control device 10 via the motor 9c, rotated around the center of the incident beam axis 1a, and set to any rotation angle. As described above, irradiation is performed at any irradiation angle and at any rotation angle; and accordingly, the irradiation can be performed in any shape on a two-dimensional flat surface perpendicular to the incident beam axis 1a at an irradiation angle from 0 degrees to 90 degrees around the body axis of the patient 4a. Next, the range shifter 7a takes in and out the plurality of the plates having the density equivalent to water and being different in thickness; and accordingly, energy of the beam 1 is attenuated to any energy, depth at which the beam 1 is stopped is changed, similarly the beam 1 is distributed in any shape of two-dimensional flat surface, and the beam 1 is irradiated.

As described above, a spot of the beam 1 is three-dimensionally arranged; and accordingly, the irradiation can be performed to the irradiation target 4b in a uniform radiation dose distribution in accordance with its three-dimensional shape. In this case, directions of recumbent position of the patient 4a (direction of head/leg, and face-down/face-up direction) on the recumbent position treatment bed 3a are changed; and accordingly, the irradiation can be performed at any angle of 360 degrees relative to the body axis of the patient. The irradiation is performed as described above in the preferred embodiment 1; and therefore, it is possible to obtain the scanning irradiation device of the charged particle beam which can perform multiple field irradiation at any irradiation angle even without using the gantry. Incidentally, the range shifter 7a is arranged at the lower stream of the second scanning electromagnet 2b in the preferred embodiment 1; however, the range shifter 7a may be installed at the lower stream or at the upper stream of the first scanning electromagnet 2a and the same effects can be obtained. Furthermore, the range shifter 7a can be eliminated by changing beam energy of the particle beam emitted by the accelerator; and the same effects can also be obtained in this case.

Preferred Embodiment 2

Figure 3:
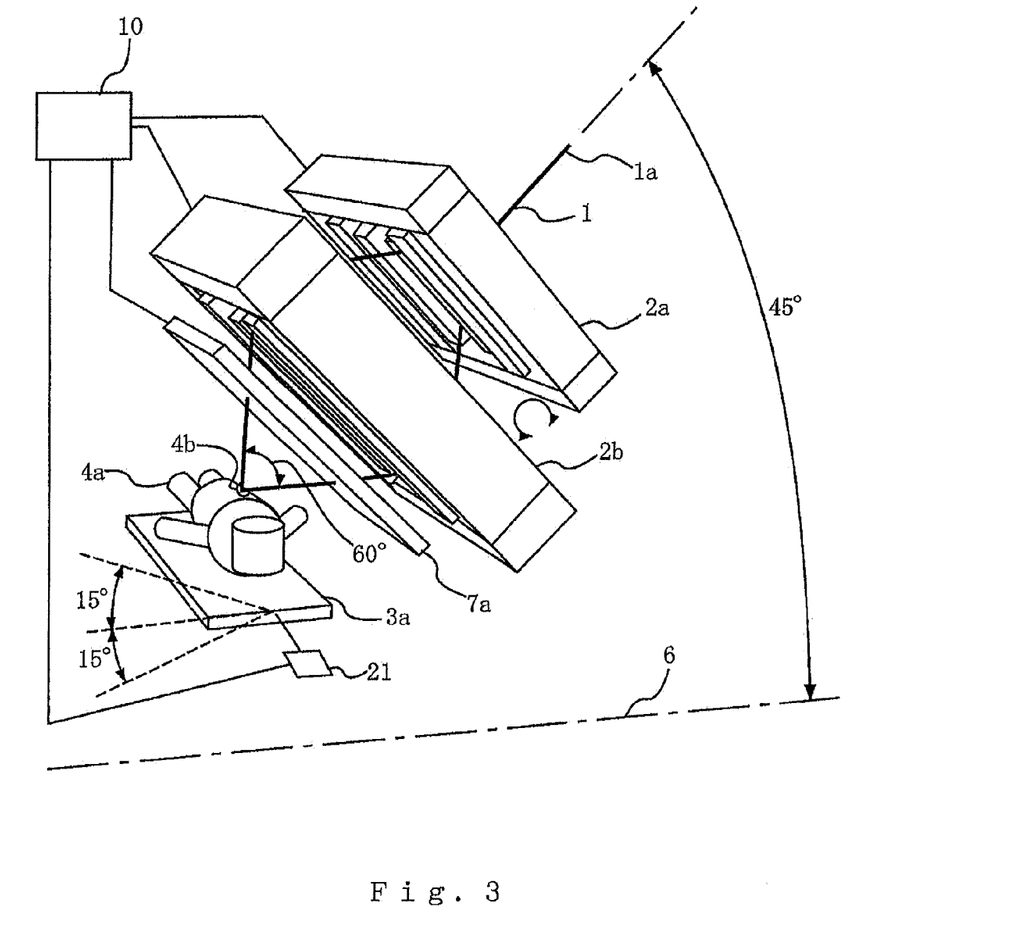
FIG. 3 is a configuration diagram showing a scanning irradiation device of a charged particle beam according to a preferred embodiment 2.

In a preferred embodiment 1, the recumbent position treatment bed 3a is kept in a horizontal position; however, if the recumbent position treatment bed is located in a range of approximately −15 degrees to +15 degrees around the body axis of the patient 4a, it is easy to fix the patient so as not to be slid down, and the recumbent position treatment bed may be inclined. FIG. 3 is a configuration diagram showing a scanning irradiation device of a charged particle beam according to a preferred embodiment 2. Incidentally, the same reference numerals are identical or equivalent portions in the respective drawings and their description will not be repeated. As shown in FIG. 3, a charged particle beam 1 is made incident from an incident beam axis angle of approximately 45 degrees relative to a floor (horizontal direction) 6. A first scanning electromagnet 2a deflects the beam 1 at any angle of a range of −30 degrees to +30 degrees (its range may be exceeded) relative to an incident beam axis 1a. A second scanning electromagnet 2b is arranged at the lower stream of the first scanning electromagnet 2a, has a beam deflection surface which is located on the same surface as that of the first scanning electromagnet 2a, and deflects the beam 1 at any angle of a range of −60 degrees to +60 degrees (its range may be exceeded) in a reverse direction to the first scanning electromagnet 2a.

An electromagnet rotation driving mechanism 20 (see FIG. 2) integrates the first scanning electromagnet 2a and the second scanning electromagnet 2b and rotates these scanning electromagnets around the incident beam axis 1a. A recumbent position treatment bed 3a is arranged by being moved to the lower stream of a range shifter 7a so that a direction orthogonal to a flat surface, the surface being in a direction perpendicular to the floor 6 and including the incident beam axis 1a, becomes a body axis direction of a patient 4a, and has a treatment bed rotation mechanism 21 capable of inclining at a range of −15 degrees to +15 degrees (its range may be exceeded) around the orthogonal direction, preferably, around the body axis. A scanning irradiation control device 10 performs control of excitation of the first and the second scanning electromagnets 2a and 2b, taking in and out of the range shifter 7a, and rotation of the electromagnet rotation driving mechanism 20; and if necessary, the scanning irradiation control device 10 performs control of rotation of the treatment bed rotation mechanism 21.

Next, the operation will be described. The intensity of excitation of the first scanning electromagnet 2a is controlled in a positive or negative direction; and accordingly, the beam 1 made incident at an incident angle of approximately 45 degrees from the floor is deflected within the deflection surface to any angle of a range of −30 degrees to +30 degrees relative to the incident beam axis 1a. Next, the intensity of excitation of the second scanning electromagnet 2b is controlled in a negative or positive direction; and accordingly, the beam 1 is deflected in a reverse direction within the deflection surface to any angle of a range of −60 degrees to +60 degrees. As described above, the beam 1 is irradiated to an irradiation target 4b of the patient within the same deflection surface at any angle of a range of −30 degrees to +30 degrees (its range may be exceeded) relative to the incident beam axis 1a.

The scanning electromagnet 2a and 2b integrally supported by a connecting support 8a are rotationally driven by a motor 9c, rotated around the center of the incident beam axis 1a, and set to any rotation angle. As described above, irradiation is performed at any irradiation angle and at any rotation angle; and accordingly, the irradiation can be performed in any shape on a two-dimensional flat surface perpendicular to the incident beam axis 1a at an irradiation angle from 0 degrees to 60 degrees around the body axis of the patient 4a. Next, by the range shifter 7a, energy of the beam 1 is attenuated to any energy, depth at which the beam 1 is stopped is changed, similarly the beam 1 is distributed in any shape of two-dimensional flat surface, and the beam 1 is irradiated.

As described above, a spot of the beam 1 is three-dimensionally arranged; and accordingly, the irradiation can be performed to the irradiation target 4b in a uniform radiation dose distribution in accordance with its three-dimensional shape. In this case, directions of recumbent position of the patient 4a on the recumbent position treatment bed 3a (direction of head/leg, and face-down/face-up direction) and the inclination of the treatment bed are changed; and accordingly, the irradiation can be performed at any angle of 360 degrees relative to the body axis of the patient. The irradiation is performed as described above in the preferred embodiment 2; and therefore, it is possible to obtain the scanning irradiation device of the charged particle beam which can perform multiple field irradiation at any irradiation angle even without using the gantry. Maximum deflection angles of the first and the second scanning electromagnets 2a and 2b are set to a range of −30 degrees to +30 degrees relative to the incident beam axis 1a; and accordingly, the first and the second scanning electromagnets 2a and 2b can be reduced in size and in cost as compared with those in which the maximum deflection angle is set to a range of −45 degrees to +45 degrees.

Preferred Embodiment 3

Figure 4:
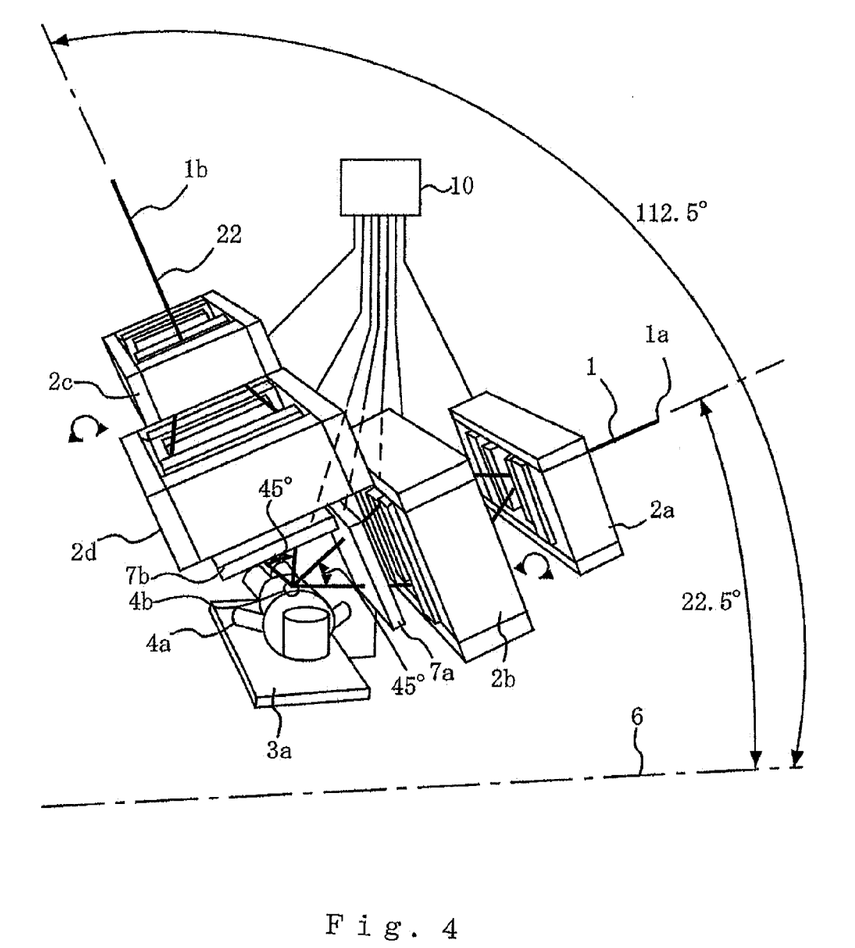
FIG. 4 is a configuration diagram showing a scanning irradiation device of a charged particle beam according to a preferred embodiment 3.

In the preferred embodiments 1 and 2, the description is made about the case where the incident beam axis 1a is only one direction; however, as shown in FIG. 4, there may be provided incident beam axes in two directions, that is, two systems. FIG. 4 is a configuration diagram showing a scanning irradiation device of a charged particle beam according to a preferred embodiment 3. In a first system, a first incident beam axis 1 is made incident from a first incident beam axis angle of approximately 22.5 degrees relative to a floor (horizontal direction) 6. A first scanning electromagnet 2a deflects the beam 1 at any angle of a range of −22.5 degrees to +22.5 degrees (its range may be exceeded) relative to a first incident beam axis 1a. A second scanning electromagnet 2b is arranged at the lower stream of the first scanning electromagnet 2a, has a beam deflection surface which is located on the same surface as that of the first scanning electromagnet 2a, and deflects the beam 1 at any angle of a range of −45 degrees to +45 degrees (its range may be exceeded) in a reverse direction to the first scanning electromagnet 2a. Further, as in FIG. 1, a first electromagnet rotation driving mechanism which integrates the first and the second scanning electromagnets 2a and 2b and rotates these scanning electromagnets around the first incident beam axis 1a is provided; and a range shifter 7a is provided at the lower stream of the second scanning electromagnet 2b.

In a second system, those similar to the first system are installed by changing an angle from a horizontal direction. That is, a second incident beam 22 is made incident from a second incident beam axis angle of approximately 112.5 degrees relative to the floor (horizontal direction) 6 within a flat surface, the surface being in a direction perpendicular to the floor and including the incident beam axis 1a. A third scanning electromagnet 2c deflects the beam 22 at any angle of a range of −22.5 degrees to +22.5 degrees (its range may be exceeded) relative to a second incident beam axis 1b. A fourth scanning electromagnet 2d has a beam deflection surface which is located on the same surface as that of the third scanning electromagnet 2c, and deflects the beam 22 at any angle of a range of −45 degrees to +45 degrees (its range may be exceeded) in a reverse direction to the third scanning electromagnet 2c. Then, similarly, a second electromagnet rotation driving mechanism which integrates the third and the fourth scanning electromagnets 2c and 2d and rotates these scanning electromagnets around the second incident beam axis 1b is provided; and a range shifter 7b is provided.

Further, a recumbent position treatment bed 3a is installed by being moved to the lower stream of the second scanning electromagnet 2b and the fourth scanning electromagnet 2d so that directions orthogonal to flat surfaces, the surfaces being in a direction perpendicular to the floor and including the first and the second incident beam axes 1a and 1b, become a body axis direction of a patient 4a. A scanning irradiation control device 10 performs control of excitation of the first, the second, the third, and the fourth scanning electromagnets 2a, 2b, 2c, and 2d; and performs control of rotation of the first and the second electromagnet rotation driving mechanisms. The scanning irradiation control device 10 may control movement of the treatment bed 3a.

Then, the first and the second scanning electromagnets 2a and 2b are configured so that a maximum deflection angle of the second scanning electromagnet 2b is larger than a maximum deflection angle of the first scanning electromagnet 2a, and a charged particle beam deflected by the first and the second scanning electromagnets 2a and 2b is a range of −22.5 degrees to +22.5 degrees (its range may be exceeded) in deflection angle from a first incident beam axis direction. The third and the fourth scanning electromagnets 2c and 2d are configured so that a maximum deflection angle of the fourth scanning electromagnet 2d is larger than a maximum deflection angle of the third scanning electromagnet 2c, and a charged particle beam deflected by the third and the fourth scanning electromagnets 2c and 2d is a range of −22.5 degrees to +22.5 degrees (its range may be exceeded) in deflection angle from a second incident beam axis direction.

A beam irradiation angle of approximately 45 degrees (range of −22.5 degrees to +22.5 degrees) by the first and the second scanning electromagnets 2a and 2b of the first system and a beam irradiation angle of approximately 45 degrees (range of −22.5 degrees to +22.5 degrees) by the third and the fourth scanning electromagnets 2c and 2d of the second system are apart as noted from FIG. 4; however, it is possible to cover a beam irradiation angle of approximately 90 degrees by combining. It is separated such that the incident beam axis angle of the first system is 22.5 degrees, whereas the incident beam axis angle of the second system is 112.5 degrees; and accordingly, it becomes possible to increase a distance between both systems and the arrangement of the both systems becomes easy.

Directions of recumbent position of the patient 4a (direction of head/leg, and face-down/face-up direction) are changed; and accordingly, an irradiation direction of the beam to an irradiation target 4b of the patient 4a can be irradiated at any angle of 360 degrees, a rotating gantry is not required, and multiple field irradiation can be performed at any irradiation angle. The scanning electromagnets 2a, 2b, 2c, and 2d of the preferred embodiment 3 can be reduced in size and increased in manufacturability, as compared with the scanning electromagnets 2a and 2b of the preferred embodiment 2.

Preferred Embodiment 4

Figure 5:
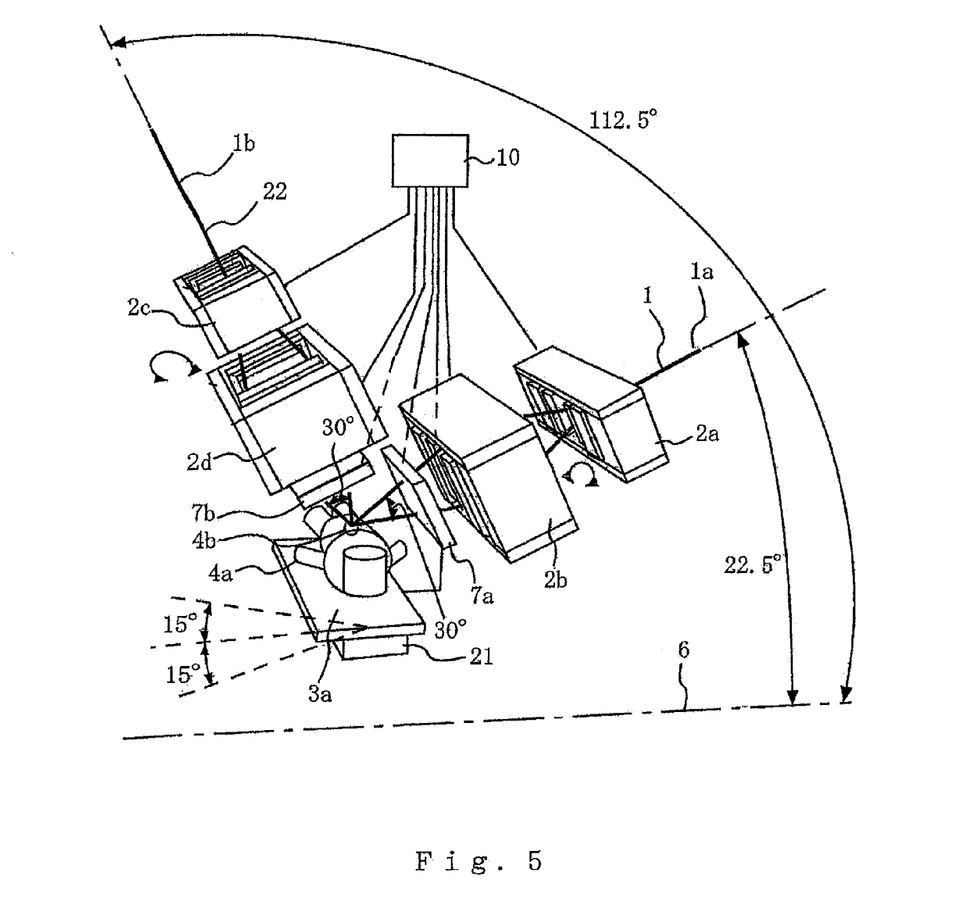
FIG. 5 is a configuration diagram showing a scanning irradiation device of a charged particle beam according to a preferred embodiment 4.

The recumbent position treatment bed 3a in the preferred embodiment 3 cannot be inclined around the axis; however, the recumbent position treatment bed 3a may be inclined around the axis as described in the preferred embodiment 2. A preferred embodiment 4 will be described mainly about different points from the preferred embodiment 3. FIG. 5 is a configuration diagram showing a scanning irradiation device of a charged particle beam according to the preferred embodiment 4. In FIG. 5, a recumbent position treatment bed 3a is arranged by being moved so that directions orthogonal to flat surfaces, the surfaces being in a direction perpendicular to the floor 6 and including the first and the second incident beam axes 1a and 1b, become a body axis direction of a patient 4a, and has a treatment bed rotation mechanism 21 capable of inclining at a range of −15 degrees to +15 degrees (its range may be exceeded) around the orthogonal direction, preferably, around the body axis. The inclination of the recumbent position treatment bed 3a can also be controlled by a scanning irradiation control device 10.

In a first system, a first incident beam axis 1 is made incident from a first incident beam axis angle of approximately 22.5 degrees relative to the floor (horizontal direction) 6. However, a first scanning electromagnet 2a deflects the beam 1 at any angle of a range of −15 degrees to +15 degrees (its range may be exceeded) relative to a first incident beam axis 1a; and a second scanning electromagnet 2b deflects the beam 1 at any angle of a range of −30 degrees to +30 degrees (its range may be exceeded) in a reverse direction to the first scanning electromagnet 2a. A range shifter 7a is provided together with a first electromagnet rotation driving mechanism.

In a second system, a second incident beam 22 is made incident from a second incident beam axis angle of approximately 112.5 degrees relative to a floor (horizontal direction) 6. However, a third scanning electromagnet 2c deflects the beam 22 at any angle of a range of −15 degrees to +15 degrees (its range may be exceeded) relative to a second incident beam axis 1b; and a fourth scanning electromagnet 2d deflects the beam 22 at any angle of a range of −30 degrees to +30 degrees (its range may be exceeded) in a reverse direction to the third scanning electromagnet 2c. A range shifter 7b is provided together with a second electromagnet rotation driving mechanism.

Then, the first and the second scanning electromagnets 2a and 2b are configured so that a maximum deflection angle of the second scanning electromagnet 2b is larger than a maximum deflection angle of the first scanning electromagnet 2a, and a charged particle beam deflected by the first and the second scanning electromagnets 2a and 2b is a range of −15 degrees to +15 degrees (its range may be exceeded) in deflection angle from a first incident beam axis direction. The third and the fourth scanning electromagnets 2c and 2d are configured so that a maximum deflection angle of the fourth scanning electromagnet 2d is larger than a maximum deflection angle of the third scanning electromagnet 2c, and a charged particle beam deflected by the third and the fourth scanning electromagnets 2c and 2d is a range of −15 degrees to +15 degrees (its range may be exceeded) in deflection angle from a second incident beam axis direction.

A beam irradiation angle of approximately 30 degrees (range of −15 degrees to +15 degrees) by the first and the second scanning electromagnets 2a and 2b of the first system and a beam irradiation angle of approximately 30 degrees (range of −15 degrees to +15 degrees) by the third and the fourth scanning electromagnets 2c and 2d of the second system are apart as noted from FIG. 5; however, it is possible to cover a beam irradiation angle of approximately 60 degrees by combining.

Directions of recumbent position of the patient 4a (direction of head/leg, and face-down/face-up direction) and the inclination of the recumbent position treatment bed 3a are changed; and accordingly, an irradiation direction of the beam to an irradiation target 4b of the patient 4a can be irradiated at any angle of 360 degrees, and a rotating gantry is not required. The first, the second, the third, and the fourth scanning electromagnets 2a, 2b, 2c, and 2d of the preferred embodiment 4 can be reduced in size and increased in manufacturability, as compared with the first, the second, the third, and the fourth scanning electromagnets 2a, 2b, 2c, and 2d of the preferred embodiment 3.

Preferred Embodiment 5

Figure 6:
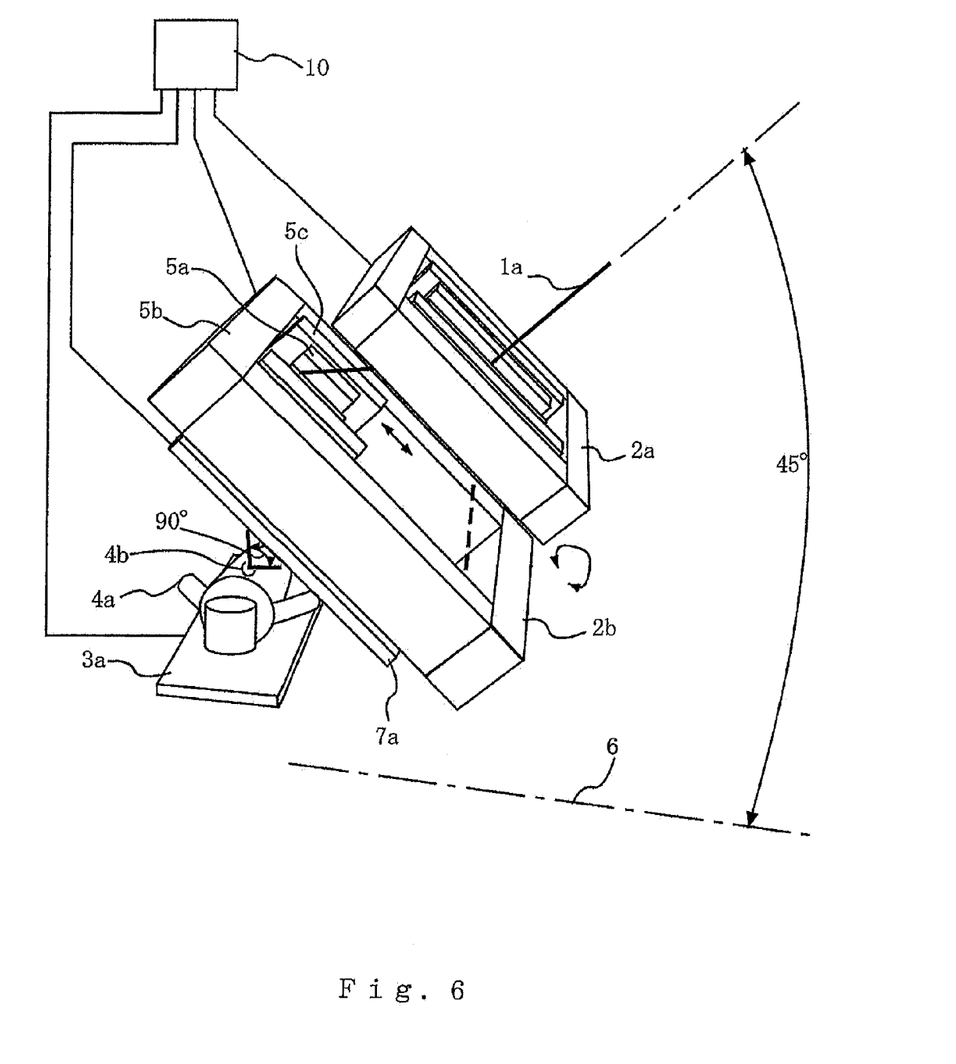
FIG. 6 is a configuration diagram showing a scanning irradiation device of a charged particle beam according to a preferred embodiment 5.

In the preferred embodiment 1, poles (electrodes) which deflect the beam in the scanning electromagnets are placed over the whole in a yoke frame and are of wide width shape; however, it may be configured by using narrow width poles which can be moved in the yoke frame. FIG. 6 is a configuration diagram showing a scanning irradiation device of a charged particle beam according to a preferred embodiment 5. In FIG. 6, a second scanning electromagnet 2b is composed of a fixed yoke frame 5b, a pair of poles 5a which are slid inside the fixed yoke frame 5b, and coils 5c wound around the poles 5a. The poles 5a are controlled by a scanning irradiation control device in response to a shaking angle of the beam; and accordingly, the poles 5a are slid in the fixed yoke frame 5b.

Figure 7:
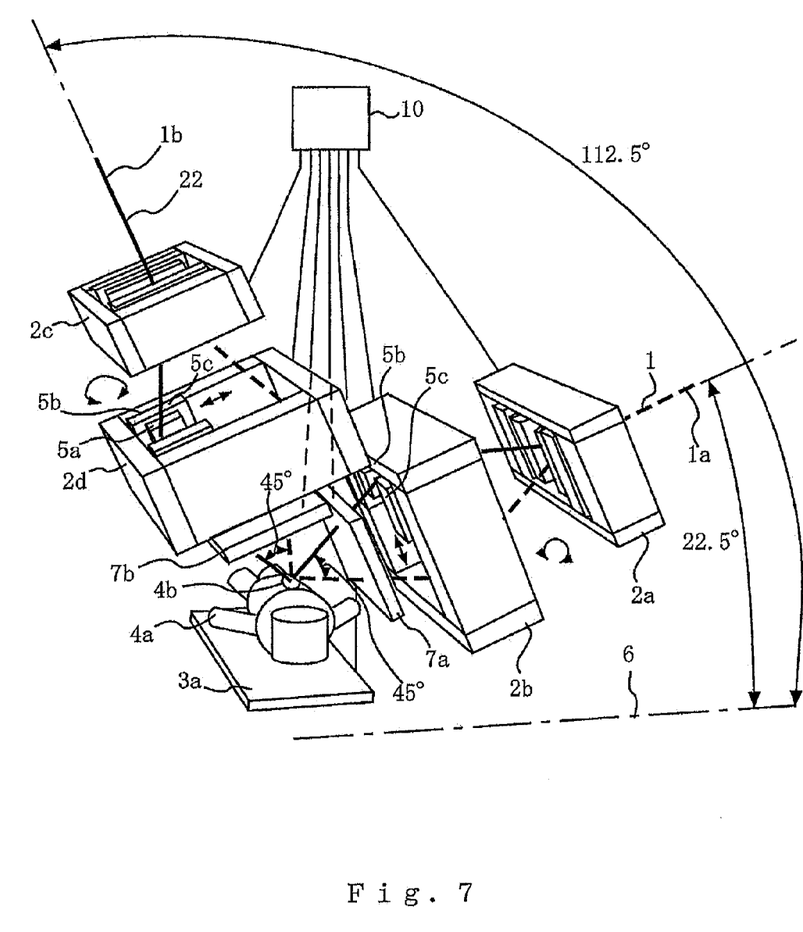
FIG. 7 is a configuration diagram showing another scanning irradiation device of a charged particle beam according to the preferred embodiment 5 of the present invention.
Figure 8:
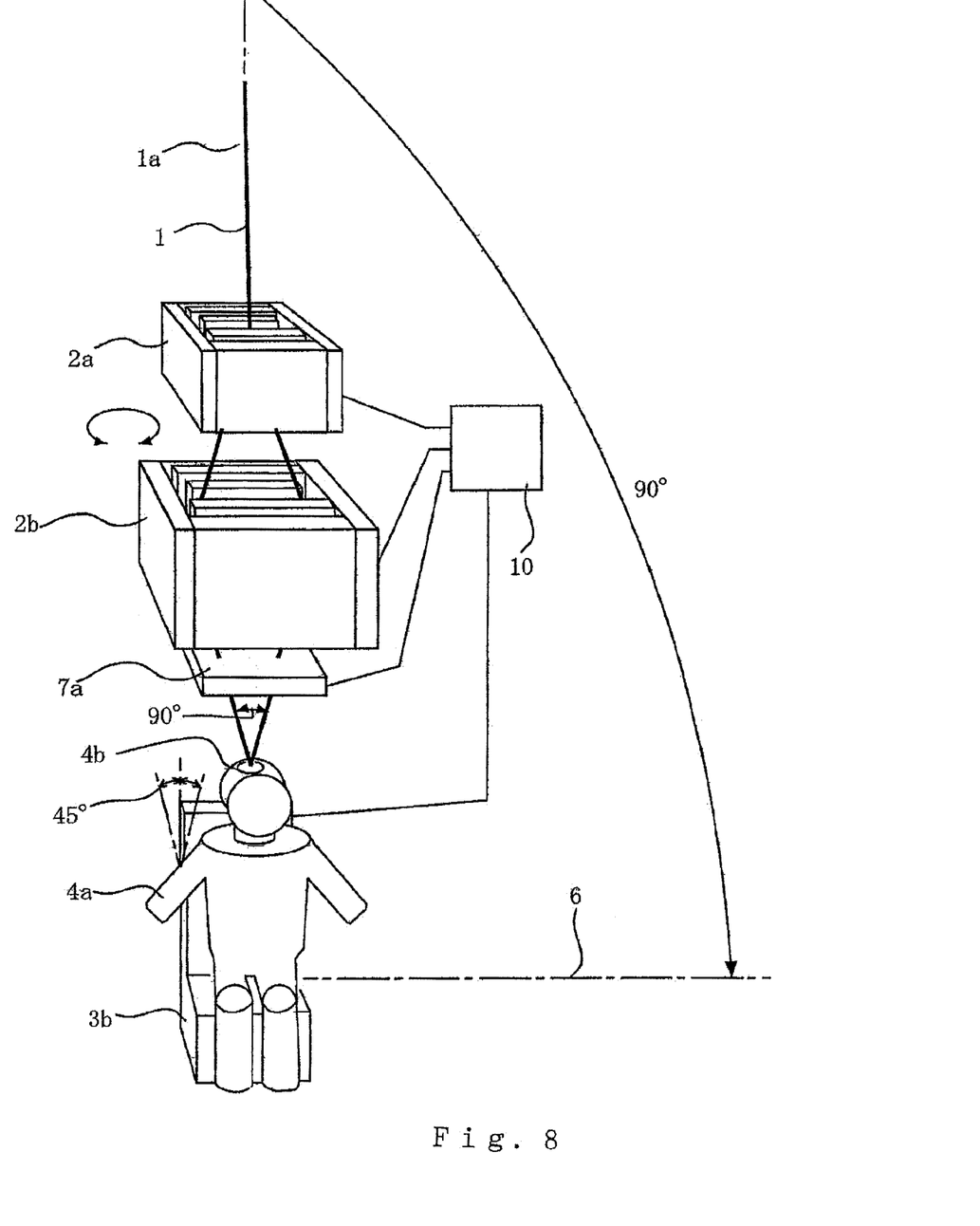
FIG. 8 is a configuration diagram showing a scanning irradiation device of a charged particle beam according to a preferred embodiment 6.
Figure 9:
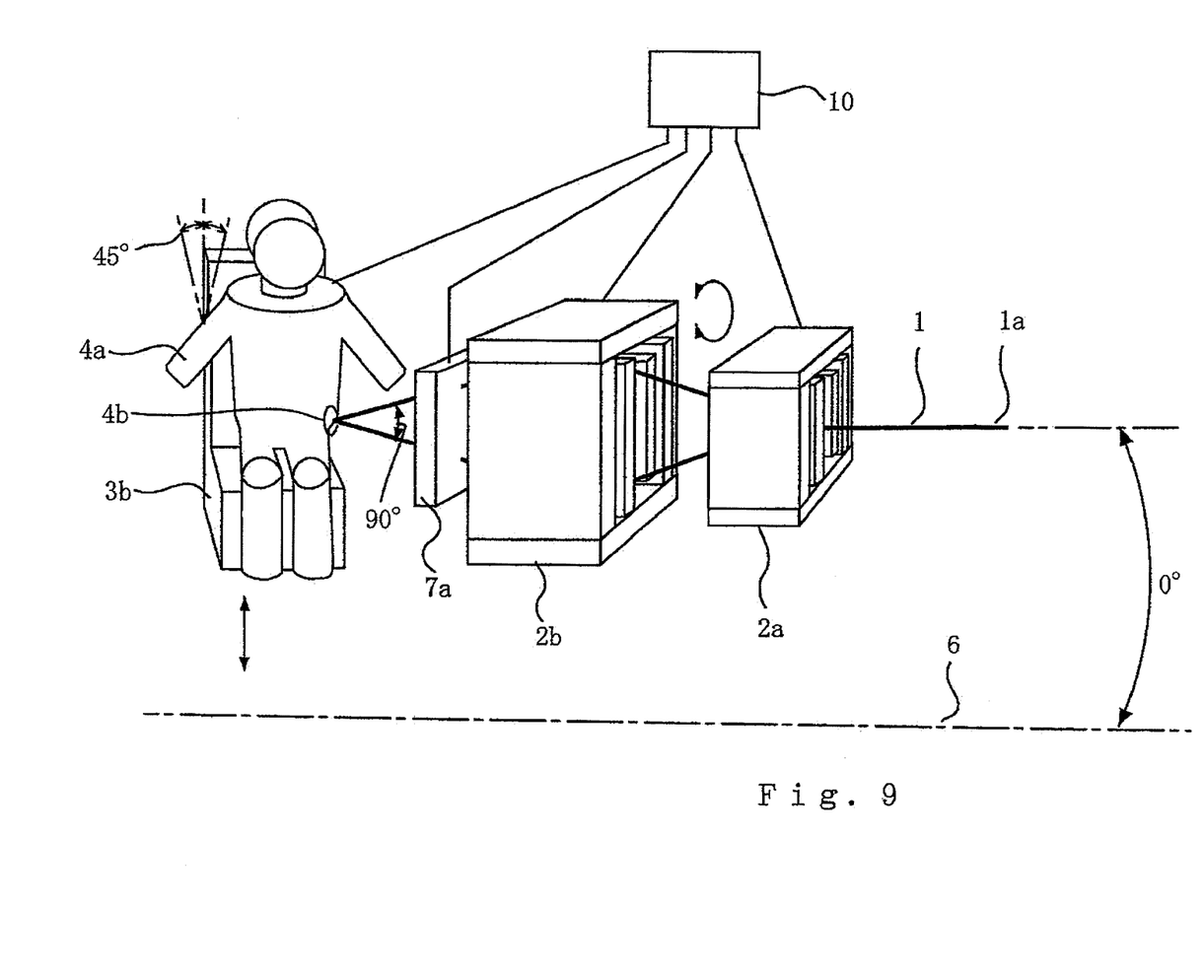
FIG. 9 is a configuration diagram showing a scanning irradiation device of a charged particle beam according to a preferred embodiment 7.

In FIG. 6, the application is made to the second scanning electromagnet 2b; however, the application can be made to at least any of the first, the second, the third, and the fourth scanning electromagnets 2a, 2b, 2c, and 2d shown in FIG. 4. FIG. 7 shows a case where the application is made to the second and the fourth scanning electromagnets 2b and 2d shown in FIG. 4. Further, the application can be made to at least any of the scanning electromagnets 2a and 2b shown in the following preferred embodiments to be described later: FIG. 8 of a preferred embodiment 6; FIG. 9 of a preferred embodiment 7; and FIG. 10 of a preferred embodiment 8. In the applied scanning electromagnets, the width of the poles can be narrowed; and therefore, the scanning electromagnet can be reduced in weight, and an inexpensive scanning irradiation device can be supplied.

Preferred Embodiment 6

In the preferred embodiments 1 to 5, the description is made about the case where the recumbent position treatment bed is used as the treatment bed on which the patient is mounted; however, a sitting position treatment bed may be used. FIG. 8 is a configuration diagram showing a scanning irradiation device of a charged particle beam according to a preferred embodiment 6. A charged particle beam 1 is made incident from an incident beam axis angle of approximately 90 degrees relative to a floor (horizontal direction) 6. A first scanning electromagnet 2a deflects the beam 1 at any angle of a range of −45 degrees to +45 degrees (its range may be exceeded) relative to an incident beam axis 1a. A second scanning electromagnet 2b is arranged at the lower stream of the first scanning electromagnet 2a, has a beam deflection surface which is located on the same surface as that of the first scanning electromagnet 2a, and deflects the beam 1 at any angle of a range of −90 degrees to +90 degrees (its range may be exceeded) in a reverse direction to the first scanning electromagnet 2a. A maximum deflection angle of the second scanning electromagnet 2a is set to be larger than a maximum deflection angle of the first scanning electromagnet 2a, so that the beam 1 is collected at an irradiation target 4b. A range shifter 7a is provided as in the preferred embodiment 1.

An electromagnet rotation driving mechanism 20 (see FIG. 2) integrates the first and the second scanning electromagnets 2a and 2b and rotates these scanning electromagnets around the incident beam axis 1a. A scanning irradiation control device 10 performs control of excitation of the first and the second scanning electromagnets 2a and 2b, rotation of the electromagnet rotation driving mechanism, and taking in and out of the range shifter 7a. A sitting position treatment bed 3b is arranged by being moved with its direction directed to the same as the front direction of the scanning irradiation device; the sitting position treatment bed 3b is installed such that a body axis at a time when a patient 4a sits on the sitting position treatment bed 3b substantially coincides with the incident beam axis 1a; and its backrest can be inclined back and forth (that is, the front and back side directions) at a range of −45 degrees to +45 degrees (its range may be exceeded). The movement and the inclination of the sitting position treatment bed 3b may be controlled by the scanning irradiation control device 10.

The first and the second scanning electromagnets are configured so that a charged particle beam deflected by the first and the second scanning electromagnets is a range of −45 degrees to +45 degrees (its range may be exceeded) in deflection angle from an incident beam axis direction. As described above, the beam 1 is irradiated to the irradiation target 4b at any angle of a range of −45 degrees to +45 degrees relative to the incident beam axis 1a. The integrally connected scanning electromagnet 2a and 2b are rotationally driven, rotated around the center of the incident beam axis 1a, and set to any rotation angle. As described above, irradiation is performed at any irradiation angle and at any rotation angle; and accordingly, the irradiation can be performed in any shape on a two-dimensional flat surface perpendicular to the incident beam axis 1a at an irradiation angle from 0 degrees to 90 degrees around the body axis of the patient.

Next, the range shifter 7a is taken in and out; and accordingly, energy of the beam 1 is attenuated to any energy, depth at which the beam 1 is stopped is changed, similarly the beam 1 is distributed in any shape of two-dimensional flat surface, and the beam 1 is irradiated. As described above, a spot of the beam 1 is three-dimensionally arranged; and accordingly, the irradiation is performed to the irradiation target in a uniform radiation dose distribution in accordance with its three-dimensional shape. In this case, a backrest of the sitting position treatment bed 3b is inclined back and forth at a range of −45 degrees to +45 degrees; and accordingly, the irradiation can be performed at any angle above a horizontal level relative to head and neck. With this configuration, there can be inexpensively supplied an irradiation device capable of performing multiple field irradiation for only head and neck for use in existing facilities which have been already provided with a fixed irradiation port.

Preferred Embodiment 7

Incidentally, in the case of using the sitting position treatment bed, the charged particle beam 1 is made incident at the incident beam axis angle of approximately 90 degrees from the floor; however, the charged particle beam may be made incident at the incident beam axis angle of approximately 0 degrees from a horizontal direction, that is, from the floor. FIG. 9 is a configuration diagram showing a scanning irradiation device of a charged particle beam according to a preferred embodiment 7. The charged particle beam 1 is made incident from an incident beam axis angle of approximately 0 degrees relative to a floor (horizontal direction) 6. First and second scanning electromagnets 2a and 2b, an electromagnet rotation driving mechanism 20, and a range shifter 7a are of the same configuration as the preferred embodiment 6. A scanning irradiation control device 10 performs control of excitation of the first and the second scanning electromagnets 2a and 2b, rotation of the electromagnet rotation driving mechanism, and taking in and out of the range shifter 7a.

A sitting position treatment bed 3b is arranged by being moved perpendicularly to the floor on a vertical two-dimensional flat surface relative to an incident beam axis with its direction being made to face to the incident beam axis; and its backrest can be inclined back and forth (that is, cross direction in incident beam axis direction) at a range of −45 degrees to +45 degrees (its range may be exceeded). Further, the sitting position treatment bed 3b can be moved up and down. The sitting position treatment bed 3b may be controlled by the scanning irradiation control device 10. As described above, irradiation is performed at any irradiation angle and at any rotation angle of the patient's front; and accordingly, the irradiation can be performed in any shape on a two-dimensional flat surface perpendicular to an incident beam axis 1a at an irradiation angle from 0 degrees to 90 degrees of the patient's front. In this case, a backrest of the sitting position treatment bed 3b is inclined back and forth at a range of −45 degrees to +45 degrees; and accordingly, the irradiation can be performed at any angle relative to the patient's front, and an irradiation device capable of performing multiple field irradiation can be supplied inexpensively.

Preferred Embodiment 8

Figure 10:
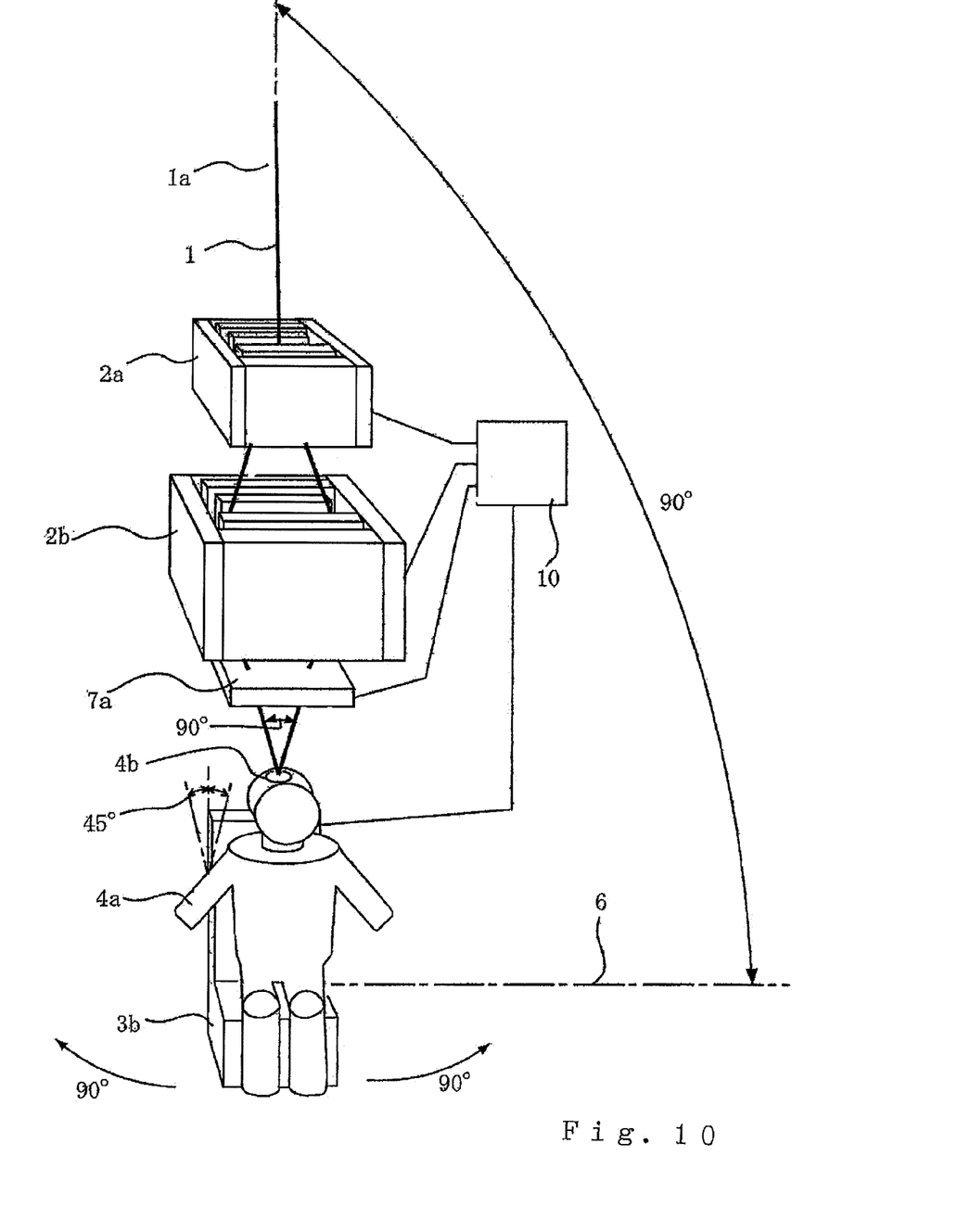
FIG. 10 is a configuration diagram showing a scanning irradiation device of a charged particle beam according to a preferred embodiment 8.

In the preferred embodiment 6, the description is made about the case of the scanning electromagnet having the electromagnet rotation driving mechanism 20. However, as shown in FIG. 10, it may be configured such that scanning electromagnets are fixed and a sitting position treatment bed 3b is rotated around an axis perpendicular to a floor. Points mainly different from the preferred embodiment 6 will be described. FIG. 10 is a configuration diagram showing a scanning irradiation device of a charged particle beam according to a preferred embodiment 8. A charged particle beam 1 is made incident from an incident beam axis angle of approximately 90 degrees elative to a floor 6. The incident beam 1 is deflected by a first scanning electromagnet 2a to any angle of a range of −45 degrees to +45 degrees (its range may be exceeded) relative to an incident beam axis 1a; and then, deflected by a second scanning electromagnet 2b to any angle of a range of −90 degrees to +90 degrees (its range may be exceeded) in a reverse direction. An electromagnet rotation driving mechanism is not provided.

A sitting position treatment bed 3b is arranged by being moved with its direction directed to the same as the front direction of the scanning irradiation device; the sitting position treatment bed 3b is installed such that a body axis at a time when a patient 4a sits on the sitting position treatment bed 3b substantially coincides with the incident beam axis 1a; and its backrest can be inclined back and forth (that is, the front and back side directions) at a range of −45 degrees to +45 degrees (its range may be exceeded). Further, rotation can be made at a range of −90 degrees to +90 degrees (its range may be exceeded) around a rotation axis in a direction perpendicular to a floor, preferably around a body axis. Movement, inclination, and rotation of the sitting position treatment bed 3b are controlled by a scanning irradiation control device 10.

As described above, the beam 1 is irradiated to an irradiation target 4b to any angle at a range of −45 degrees to +45 degrees (its range may be exceeded) relative to the incident beam axis 1a. In this case, the sitting position treatment bed 3b has a backrest which is inclined back and forth at a range of −45 degrees to +45 degrees (its range may be exceeded), and the sitting position treatment bed 3b is rotated at a range of −90 degrees to +90 degrees (its range may be exceeded) around a rotation axis in a direction perpendicular to the floor; and accordingly, the scanning electromagnets are not required to rotate, the same effects as the preferred embodiment 6 can be obtained, and an inexpensive irradiation device can be obtained.

While the presently preferred embodiments of the present invention have been shown and described. It is to be understood that these disclosures are for the purpose of illustration and that various changes and modifications may be made without departing from the scope of the invention as set forth in the appended claims.

What is claimed is:

1. A scanning irradiation device of a charged particle beam, comprising:
   a first scanning electromagnet and a second scanning electromagnet located at the lower stream of the first scanning electromagnet, whose deflection surfaces of a charged particle beam are the same, and whose excitations are controlled so as to bend, in reverse directions of each other, the charged particle beam having an incident beam axis angle of approximately 45 degrees relative to a horizontal direction;
   an electromagnet rotation driving mechanism which integrates the first and the second scanning electromagnets and rotates these scanning electromagnets around the incident beam axis;
   a scanning irradiation control device which performs control of the excitations of the first and the second scanning electromagnets and performs control of the rotation of the electromagnet rotation driving mechanism; and
   a treatment bed which is moved to the lower stream of the second scanning electromagnet and is installed so that a body axis direction of a patient is in a direction orthogonal to a flat surface, the surface being in a direction perpendicular to a floor and including the incident beam axis,
   the first and the second scanning electromagnets are configured such that a maximum deflection angle of the second scanning electromagnet is larger than a maximum deflection angle of the first scanning electromagnet, and the charged particle beam deflected by the first and the second scanning electromagnets can be obtained at a range of −45 degrees to +45 degrees in deflection angle from the incident beam axis direction.

2. The scanning irradiation device of the charged particle beam according to claim 1, wherein the treatment bed can be rotated at a range of −15 degrees to +15 degrees around an axis orthogonal to the flat surface, the surface being in the direction perpendicular to the floor and including the incident beam axis, and the first and the second scanning electromagnets are configured so that the charged particle beam deflected by the first and the second scanning electromagnets can be obtained at a range of −30 degrees to +30 degrees in deflection angle from the incident beam axis direction.

3. The scanning irradiation device of the charged particle beam according to claim 1, wherein the scanning electromagnets are each composed of a fixed yoke frame having a rectangle shape and a pair of poles wound by coils which are arranged inside the fixed yoke frame and slid in the fixed yoke frame, the pair of poles being slid in the fixed yoke frame in response to the deflection angle of the charged particle beam.

4. A scanning irradiation device of a charged particle beam, comprising:
   a first scanning electromagnet and a second scanning electromagnet located at the lower stream of the first scanning electromagnet, whose deflection surfaces of a charged particle beam are the same, and whose excitations are controlled so as to bend, in reverse directions of each other, the charged particle beam having a first incident beam axis angle of approximately 22.5 degrees relative to a horizontal direction;
   a first electromagnet rotation driving mechanism which integrates the first and the second scanning electromagnets and rotates these scanning electromagnets around the first incident beam axis;
   a third scanning electromagnet and a fourth scanning electromagnet located at the lower stream of the third scanning electromagnet, whose deflection surfaces of a charged particle beam are the same, and whose excitations are controlled so as to bend, in reverse directions to each other within a flat surface, the charged particle beam having a second incident beam axis angle of approximately 112.5 degrees relative to the horizontal direction, the surface being in a direction perpendicular to a floor and including the second incident beam axis;
a second electromagnet rotation driving mechanism which integrates the third and the fourth scanning electromagnets and rotates these scanning electromagnets around the second incident beam axis;
a scanning irradiation control device which performs control of the excitations of the first, the second, the third, and the fourth scanning electromagnets, and performs control of the rotations of the first and the second electromagnet rotation driving mechanisms; and
a treatment bed which is moved to the lower stream of the second and the fourth scanning electromagnets and is installed so that a body axis direction of a patient is in a direction orthogonal to a flat surface, the surface being in a direction perpendicular to the floor and including the incident beam axis, wherein
the first and the second scanning electromagnets are configured so that a maximum deflection angle of the second scanning electromagnet is larger than a maximum deflection angle of the first scanning electromagnet, and the charged particle beam deflected by the first and the second scanning electromagnets can be obtained at a range of −22.5 degrees to +22.5 degrees in deflection angle from the first incident beam axis direction, and
the third and the fourth scanning electromagnets are configured so that a maximum deflection angle of the fourth scanning electromagnet is larger than a maximum deflection angle of the third scanning electromagnet, and the charged particle beam deflected by the third and the fourth scanning electromagnets can be obtained at a range of −22.5 degrees to +22.5 degrees in deflection angle from the second incident beam axis direction.

5. The scanning irradiation device of the charged particle beam according to claim 4, wherein the treatment bed can be rotated at a range of −15 degrees to +15 degrees around axes orthogonal to the flat surfaces, the surfaces being in the direction perpendicular to the floor and including the incident beam axes, the first and the second scanning electromagnets are configured so that the charged particle beam deflected by the first and the second scanning electromagnets can be obtained at a range of −15 degrees to +15 degrees in deflection angle from the first incident beam axis direction, and the third and the fourth scanning electromagnets are configured so that the charged particle beam deflected by the third and the fourth scanning electromagnets can be obtained at a range of −15 degrees to +15 degrees in deflection angle from the second incident beam axis direction.

6. The scanning irradiation device of the charged particle beam according to claim 4, wherein the scanning electromagnets are each composed of a fixed yoke frame having a rectangle shape and a pair of poles wound by coils which are arranged inside the fixed yoke frame and slid in the fixed yoke frame, the pair of poles being slid in the fixed yoke frame in response to the deflection angle of the charged particle beam.

7. A scanning irradiation device of a charged particle beam, comprising:
a first scanning electromagnet and a second scanning electromagnet located at the lower stream of the first scanning electromagnet, whose deflection surfaces of a charged particle beam are the same, and whose excitations are controlled so as to bend, in reverse directions to each other, the charged particle beam having an incident beam axis angle of approximately 90 degrees relative to a horizontal direction;
an electromagnet rotation driving mechanism which integrates the first and the second scanning electromagnets and rotates these scanning electromagnets around the incident beam axis;
a scanning irradiation control device which performs control of the excitations of the first and the second scanning electromagnets and performs control of the rotation of the electromagnet rotation driving mechanism; and
a sitting position treatment bed which is arranged in a direction perpendicular to a floor at the lower stream of the second scanning electromagnet, and in which a backrest can be inclined back and forth at a range of −45 degrees to +45 degrees, wherein
the first and the second scanning electromagnets are configured so that a maximum deflection angle of the second scanning electromagnet is larger than a maximum deflection angle of the first scanning electromagnet, and the charged particle beam deflected by the first and the second scanning electromagnets can be obtained at a range of −45 degrees to +45 degrees in deflection angle from the incident beam axis direction.

8. The scanning irradiation device of the charged particle beam according to claim 7, wherein the scanning electromagnets are each composed of a fixed yoke frame having a rectangle shape and a pair of poles wound by coils which are arranged inside the fixed yoke frame and slid in the fixed yoke frame, the pair of poles being slid in the fixed yoke frame in response to the deflection angle of the charged particle beam.

9. A scanning irradiation device of a charged particle beam, comprising:
a first scanning electromagnet and a second scanning electromagnet located at the lower stream of the first scanning electromagnet, whose deflection surfaces of a charged particle beam are the same, and whose excitations are controlled so as to bend, in reverse directions to each other, the charged particle beam having an incident beam axis angle of approximately 0 degrees relative to a horizontal direction;
an electromagnet rotation driving mechanism which integrates the first and the second scanning electromagnets and rotates these scanning electromagnets around the incident beam axis;
a scanning irradiation control device which performs control of the excitations of the first and the second scanning electromagnets and performs control of the rotation of the electromagnet rotation driving mechanism; and
a sitting position treatment bed which is faced to the charged particle beam and arranged in a direction perpendicular to a floor at the lower stream of the second scanning electromagnet, and in which a backrest can be inclined back and forth at a range of −45 degrees to +45 degrees, wherein
the first and the second scanning electromagnets are configured so that a maximum deflection angle of the second scanning electromagnet is larger than a maximum deflection angle of the first scanning electromagnet, and the charged particle beam deflected by the first and the second scanning electromagnets can be obtained at a range of −45 degrees to +45 degrees in deflection angle from the incident beam axis direction.

10. The scanning irradiation device of the charged particle beam according to claim 9, wherein the scanning electromagnets are each composed of a fixed yoke frame having a rectangle shape and a pair of poles wound by coils which are arranged inside the fixed yoke frame and slid in the fixed yoke frame, the pair of poles being slid in the fixed yoke frame in response to the deflection angle of the charged particle beam.

11. A scanning irradiation device of a charged particle beam, comprising:
- a first scanning electromagnet and a second scanning electromagnet located at the lower stream of the first scanning electromagnet, whose deflection surfaces of a charged particle beam are the same, and whose excitations are controlled so as to bend, in reverse directions to each other, the charged particle beam having an incident beam axis angle of approximately 90 degrees relative to a horizontal direction;
- a scanning irradiation control device which performs control of the excitations of the first and the second scanning electromagnets; and
- a sitting position treatment bed which is arranged in a direction perpendicular to a floor at the lower stream of the second scanning electromagnet, and in which a backrest can be inclined back and forth at a range of −45 degrees to +45 degrees and can be rotated at a range of −90 degrees to +90 degrees around a rotation axis in the direction perpendicular to the floor, wherein
- the first and the second scanning electromagnets are configured so that a maximum deflection angle of the second scanning electromagnet is larger than a maximum deflection angle of the first scanning electromagnet, and the charged particle beam deflected by the first and the second scanning electromagnets can be obtained at a range of −45 degrees to +45 degrees in deflection angle from the incident beam axis direction.

12. The scanning irradiation device of the charged particle beam according to claim 11, wherein the scanning electromagnets are each composed of a fixed yoke frame having a rectangle shape and a pair of poles wound by coils which are arranged inside the fixed yoke frame and slid in the fixed yoke frame, the pair of poles being slid in the fixed yoke frame in response to the deflection angle of the charged particle beam.

* * * * *